United States Patent [19]

Pao

[11] Patent Number: 4,885,004
[45] Date of Patent: Dec. 5, 1989

[54] ROTATING STYLUS CYSTITOME

[76] Inventor: David S. C. Pao, 95 Highpoint Dr., Churchville, Pa. 18966

[21] Appl. No.: 344,414

[22] Filed: Apr. 25, 1989

Related U.S. Application Data

[63] Continuation of Ser. No. 114,117, Oct. 27, 1987, abandoned, which is a continuation-in-part of Ser. No. 83,897, Aug. 6, 1987, Pat. No. 4,766,896, which is a continuation of Ser. No. 822,122, Jan. 24, 1986, abandoned.

[51] Int. Cl.$^4$ .............................................. A61B 17/32
[52] U.S. Cl. ..................................... 604/22; 128/305; 30/317
[58] Field of Search .......................... 604/22; 128/305; 30/317, 310, 321

[56] References Cited

U.S. PATENT DOCUMENTS

| 3,922,784 | 12/1975 | Prince et al. | 30/329 X |
| 4,301,802 | 11/1981 | Poler | 128/303.14 |
| 4,574,802 | 3/1986 | Straub et al. | 128/305 |
| 4,763,651 | 8/1988 | Kaufman et al. | 128/305 X |

FOREIGN PATENT DOCUMENTS 165657 12/1985 European Pat. Off. .
3205959A 2/1982 Fed. Rep. of Germany .

OTHER PUBLICATIONS

Janet C. Witzleben; "Describe New Method, Surgical Knife for Anterior Capsulotomy"; *Ophthalmology Times;* vol. 9, No. 18, 9/15/84.
Frederick H. Daviddorf, Donald A. Keller; "Atlas of Eye Surgery and Related Anatomy"; *Keller Publishing Co.;* pp. 29-34 and 147-166 (1978).

*Primary Examiner*—Michael H. Thaler
*Attorney, Agent, or Firm*—Woodcock, Washburn, Kurtz, Mackiewicz & Norris

[57] ABSTRACT

Novel surgical instruments for cutting soft tissues, and the like, are provided. The instruments include an elongated shaft having a cutting member rotatably mounted to the shaft and disposed to slide against a substantially planar surface of the shaft. The stylus and planar surfaces are disposed to provide smooth rotating action to the cutting instrument during such surgical procedures as cataract operations. The instruments also preferably include cutting blades having blade faces forming acute angles of less than 50°, for providing sharp cutting surfaces even when the instruments are tilted by a surgeon while accessing tight surgical areas.

17 Claims, 2 Drawing Sheets

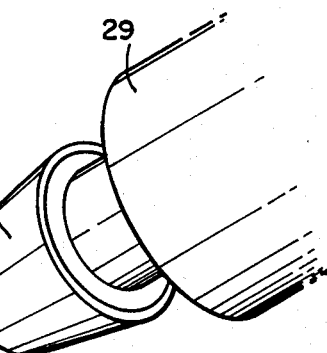
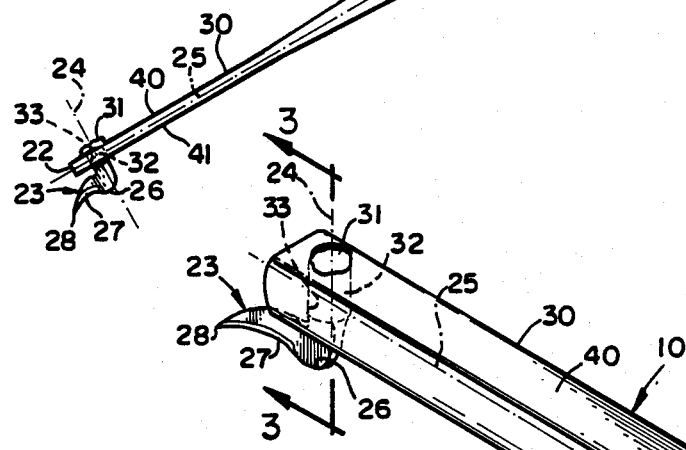
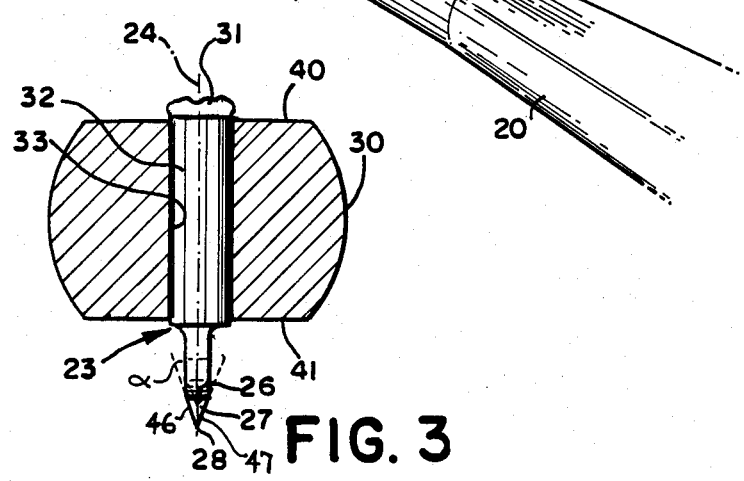

ROTATING STYLUS CYSTITOME

CROSS REFERENCE TO RELATED APPLICATIONS

This application is a continuation of application Ser. No. 114,117, abandoned, which is continuation-in-part of my copending application, Ser. No. 083,897, filed Aug. 6, 1987, now U.S. Pat. No. 4,766,896 for "Anterior Capsulotomy Procedures", which in turn, is a continuation of my application, Ser. No. 822,122, filed Jan. 24, 1986, abandoned. These commonly-owned applications are hereby incorporated by reference.

FIELD OF THE INVENTION

This invention is directed to improved surgical cutting devices and, in particular, to improved cystitomes having freely rotating blades for performing anterior capsulotomy.

BACKGROUND OF THE INVENTION

An anterior capsulotomy procedure is one wherein the surface of the anterior capsule of the eye is broken or partially removed allowing access to the lens interior of the eye. Such a procedure is commonly performed as part of a cataract removal. The current surgical procedures for anterior capsulotomy include the Christmastree technique, the beer-can opener technique, etc. See F. H. Davidtorf et al, *Atlas of Eye Surgery and Related Anatomy*, Keller Publishing Company, pp. 29–34, 147–166, Vol. 128, No. 305 (1978). These techniques are deficient, however, since they produce flaps of anterior capsule material, called tags, which remain to obscure the surgeon's view of the capsule and can interfere with the removal of the lens and/or cortical material and the placement of an artificial lens. The tears produced by these procedures can also allow an implanted artificial lens to slip or escape entirely from the capsule.

Cauterization techniques have also been employed for surgically entering a lens capsule in the course of a cataract operation. See S. Polar, U.S. Pat. No. 4,301,802. Polar discloses a cauterizing tool in which the localizing working surface of a cauterizing electrode is at an offset end of an elongate tubular body which may be of hypodermic needle proportions. Cauterization devices, such as Polar's, permit an electric current to be passed between the electrode and a receiving electrode contacting a patient's body elsewhere. The current coagulates the anterior capsule, making it extremely friable. Although cauterization techniques minimize the number of tags and tears, these devices can produce capsule shrinkage and rupturing and adjacent zonules due to excessive heat produced by the electrode. Additionally, this equipment is more expensive than mechanical cutting devices and can produce electrical interference in electrical monitoring equipment in the operating room.

There are commercially available cystitomes that do not produce capsule shrinkage. See Geuder, German Patent No. 3205959, issued Sept. 1, 1983, and Schmidt, European Patent Application No. 165657. The Geuder patent discloses an instrument employing a cutter which operates via a wire system within a lance to make a desired incision. Schmidt discloses a rotating stylus cystitome having a knife blade configured in an offset manner, whereby the blade cutting edge is spaced from and directed toward the blade pivot axis, thereby providing a castering action of the blade in response to movement of the shaft tip. See also J. C. Witzleben, *Describe New Method, Surgical Knife for Anterior Capsulotomy*, Reprinted from *Ophthalmology Times*, Vol. 9, No. 18, Sept. 15, 1984.

The rotating stylus cystitome, in its earliest configurations, has presented some difficulties during surgery, since the crimped end of the rotating cutting member can often bind and occasionally cause the stylus to fail to rotate completely. This has been attributed to the fact that the rigid shaft or cannula member is round and the rotating stylus tends to follow the curvature of the hole in the round cannula in which it is disposed. The sliding metal surfaces of the shaft and stylus can cause the rotating stylus to move vertically up and down as it is rotated. In addition, the angle between the faces of the cutting blade has often been too large to provide clean and efficient cutting of the anterior capsule, especially when the cutting blade is significantly deviated from a position perpendicular to the plane of the capsule.

Accordingly, there is a need for an improved cystitome having a construction which provides for efficient cutting of the anterior capsule for cataract operations. There is also a need for a rotating stylus cystitome that provides smoother rotation during surgery.

SUMMARY OF THE INVENTION

This invention provides a surgical instrument for cutting soft tissue, and the like, and includes a rotating stylus mounted to a rigid shaft. The shaft is provided with at least one planar surface disposed on the shaft, preferably on a surgically superior surface of the shaft, to provide smooth rotation to a capped or crimped portion of the stylus. The vertical motion of the cutting edge is therefore minimized and cataract surgery is greatly facilitated. The planar surface is disposed substantially perpendicularly to a central axis of an aperture located in an end portion of the rigid shaft.

This invention also discloses blade configurations, including a sharp, acute angle between the faces of the blade, to provide sound severing ability even when the instrument is tilted and rotated inside the anterior capsule during cataract surgery.

The operation of the stylus requires continuous rotation to effect the removal of a portion of the anterior capsule. It has been discovered that if the angle between the blade faces exceeds 50, the blade will often lose its ability to cut even in the middle of an operation. The risk of infection and increased trauma in the eye associated with switching to a sharper instrument during sensitive cataract surgery on an anesthetized patient is not one many surgeons would take. Accordingly, a sharper acute angle between the blade faces can limit this risk and restore confidence in the surgeons who use these devices.

An improved rotating stylus cystitome is disclosed which provides for smoother operation during surgical procedures. The cystitome provides for safer and less traumatic cataract operations, since it is relatively free of erratic motion.

Other improvements presented by this invention include providing an additional planar surface to the surgically inferior portion of the shaft for enabling the cutting member to rotate unimpeded. This additional planar surface reduces the tendency of the inferior portion of the stylus to ride vertically as it rotates. In this embodiment, because both the superior and the inferior surfaces of the shaft are planar, almost all vertical movement of the cutting member is eliminated and the tendency of the stylus to catch within the shaft is minimized.

It is, therefore, an object of this invention to provide a rotating stylus cystotome having smoother operation.

It is another object of this invention to provide a surgical cutting device that provides more efficient cutting capability without binding.

It is still another object of this invention to provide a rotating stylus cystitome having a more severe angle of cutting for permitting easier severing of soft tissue.

It is still another object of this invention to provide a rotating stylus cystitome having an extended heel portion for creating stress in the anterior capsule for easier cutting.

With these and other objects in view, which will become apparent to one skilled in the art as the description proceeds, this invention resides in the novel construction, combination, arrangement of parts and methods substantially as hereinafter described and more particularly defined by the attached claims.

BRIEF DESCRIPTION OF THE DRAWINGS

The accompanying drawings illustrate a complete embodiment of the invention according to the best mode so far devised for the practical application of the principles thereof, and in which:

FIG. 1: is a partial perspective view of the preferred rotating stylus cystitome of this invention;

FIG. 2: is an enlarged view of the end portion of the rotating stylus cystitome of FIG. 1 illustrating the cutting member of the cystitome incident upon an anterior capsule; and FIG. 3: is an enlarged cross-sectional view taken through line 3—3 of FIG. 2, illustrating the cutting member disposed in an aperture of the shaft;

DETAILED DESCRIPTION OF THE INVENTION

Figure 4:
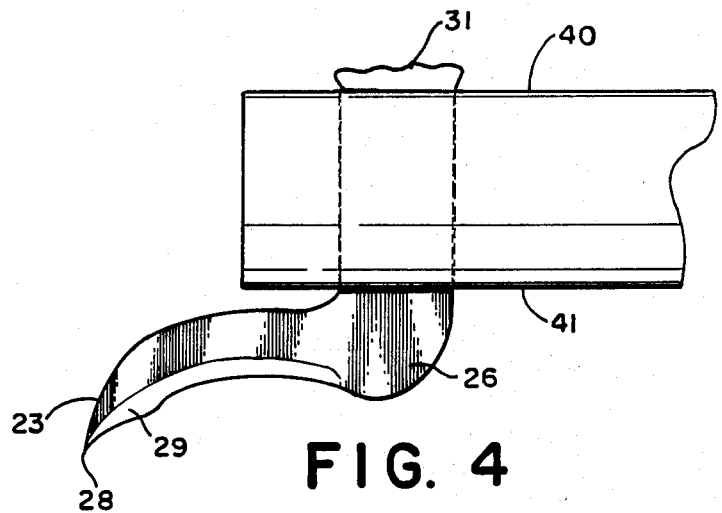
FIG. 4: is an enlarged side view of a rotating stylus cystitome embodiment illustrating the heel portion disposed on the cutting member above the sharp point.

In accordance with the teachings of this invention, improved surgical instruments for cutting soft tissue, and the like, are disclosed. The instruments include an elongated rigid shaft having an end portion with an aperture transversely disposed therethrough. The end portion has a substantially planar surface disposed substantially perpendicularly to a central axis of the aperture. Additionally, a cutting member is rotatably mounted to the shaft of these instruments through the aperture and disposed to slide against the substantially planar surface.

In a more preferred design, the surgical instruments include a planar surface disposed on a surgically superior surface of the shaft. The cutting member of such a preferred designed can include a swivel portion disposed through the aperture and an outwardly facing knife portion laterally disposed from the swivel portion. This knife portion can comprise a cutting blade terminating in a sharp point for piercing and cutting the anterior capsule during cataract surgery. Also included in the most preferred designs is a heel portion disposed generally below the swivel portion. This heel portion is disposed to provide a tensile force in the tissue between the heel portion and the sharp point when the heel portion and the sharp point are engaged with the tissue for cutting.

In order to keep the cutting member from falling out of the aperture, the superior end of the stylus can be crimped or capped. The crimped or capped portion is preferably slidably disposed on the planar superior surface of the shaft. The shaft can also include a substantially planar surface on its inferior, or lower surface to provide smoother rotation for the top portion of the cutting member as it rotates on the shaft.

The cutting blade of this invention can comprise a concave configuration between the heel and the sharp point and should also include at least two blade faces forming an acute angle therebetween. Preferably, this acute angle is less than about 50 degrees, more preferably less than 40 degrees, and most preferably less than 30 degrees. In a favored design, the heel 26 extends from the cutting member, so that it can directly contact the surface of the tissue. As used herein, when the heel 26 is described a being "below" the sharp point, it extends in the inferior direction from its "elbow" position below the swivel portion 32 so that its lowest point is further than the sharp point from the central longitudinal axis 25 of the shaft 20. Similarly, when the heel 26 is described as being "above" the sharp point, the heel 26 is disposed closer to this axis. Finally, the shaft of the surgical instrument can be cannulated to provide the necessary fluids through the end of the shaft during surgery.

Referring now to the figures, and particularly to FIG. 1, a surgical instrument 10 having a rotating cutting member, hereinafter referred to as the stylus 23. The surgical instrument 10 includes an elongated rigid shaft 20 having an end portion 22 with an aperture 33 transversely disposed therethrough. The end portion 22 includes a substantially planar surface 41 disposed substantially perpendicularly to a central axis of the aperture 24, which in this case is also the axis of rotation for the cutting member or stylus 23.

The cutting member or stylus 23 is rotatably mounted to the shaft 20 through said aperture 33 and disposed to slide against the planar surface 41. The stylus 23 preferably extends transversely from end portion 22 opposite a superior side 40 of said end portion 22 of the instrument and is pivotally mounted in the end portion 22 of the instrument so as to freely rotate 360° about an axis coexistent with axis 24 extending perpendicularly to a central longitudinal axis 25 of the shaft 20. The preferred stylus 23 has multiple curves and includes a tensioning heel 26 formed by a convex butt edge, a blade 27 formed by a connecting concave edge and a piercing sharp point 28 includes with the blade 27. Alternatively, another blade shape without a heel, such as a sickle shape, might be less advantageously employed. Either blade shape is sharpened sufficiently to slice the capsule producing a smoothly cut incision.

The preferred instrument is coupled with a handle connector 21 to suitable handle 29, such as a conventional irrigating handpiece or syringe, for manipulating the cystitome and for introducing fluid into a cannula within the shaft, primarily for irrigating the stylus 23 to assure smooth and easy rotation.

The heel 26 is preferably disposed generally below the swivel portion 32, preferably to provide a tensile force in the tissue at least between the heel portion 26 and the sharp point 28 when the heel portion 26 and the sharp point 28 are engaged with the tissue for cutting.

The cutting member or stylus 23 can also comprise a crimped or capped portion 31 disposed substantially perpendicularly to a central axis of rotation, shown as axis 24, of the cutting member. The crimped portion 32 should include a dimension larger than the diameter of the aperture so that the stylus 23 will not dislocate during the operation of the instrument.

The crimped portion of the stylus 23 preferably is slidably disposed to rotate on a surgically superior surface 40 of the end portion 22 of the rigid shaft 20. This superior surface 40 can also be substantially planar to minimize the vertical motion of the stylus during cutting.

Figure 5:
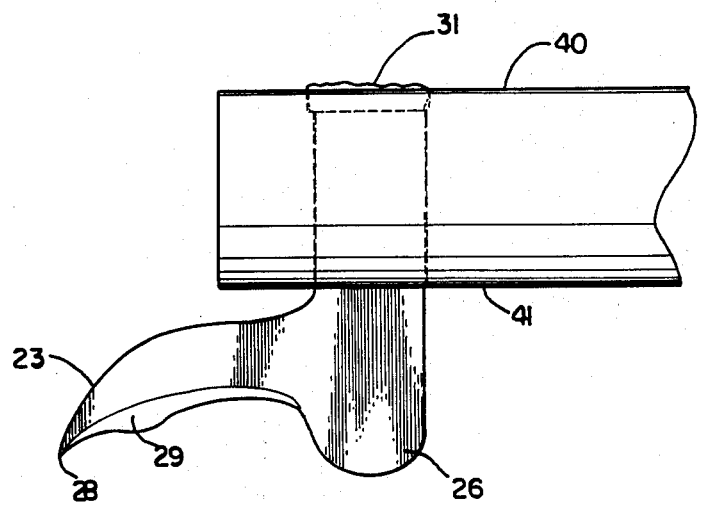
FIG. 5: is an enlarged side view of another rotating stylus cystitome wherein the heel portion is disposed on the cutting member below the sharp point and the crimped portion is disposed in a recessed portion of the rigid shaft.

If a round cap is employed, instead of a crimped portion, on the superior end of the stylus 23, this planar surface may be omitted since the cap would provide 360° of support and fairly stable rotation even on the alternating concave-convex edge of a transverse hole in a round shaft. Alternatively, the crimped portion 31 can be disposed in a recessed portion, as illustrated in FIG. 5, of the shaft 20 so as to be partially or entirely below the superior surface 40. In such a design, the bottom of the recessed portion, adjacent the crimped portion 31, would preferably have a planar surface and the superior surface 40 of the shaft 20 could be configured in, for example, a more rounded shape. It is also expected that the cutting member could be rotatably disposed with the shaft 20 by using such known mechanical means as a ball and socket joint or bearing arrangement, whereby the cutting member would be attached to the shaft 20, but allowed to move freely in a 360° rotation.

The blade portion 27 preferably comprises a slight concave configuration between the heel 26 and the sharp point 28. The cutting blade 27 includes at least two blade faces 46 and 47 which form an acute angle "α" therebetween. This acute angle "α" is designed to be less than about 50 degrees, preferably less than about 40 degrees and, most preferably, less than 30 degrees. The angle between the two blade faces 46 and 47 must be small enough to provide a sharp surface for facilitating cutting but it is often limited by manufacturing tolerances. If the angle "α" is too large, i.e., over 50°, the cutting blade can fail to cut when tilted significantly from a position perpendicular to the plane of the tissue, i.e., when rotating the stylus 23 during cutting of the anterior capsule.

It is expected that the cutting portion 27 could comprise an outwardly facing convex portion 29 disposed next to the sharp point 28. This feature would provide greatly facilitated piercing and slicing during the initial stages of severing the anterior capsule.

The sharp point 28 is designed to pierce the anterior capsule, at a first point and is inserted sufficiently for the heel 26 to contact and apply a downward pressure at a second point adjoining and spaced from the first point. In use, the heel 26 first tensions a portion of the capsule which is then cut by the trailing blade 27. Thus, the portion of the capsule beneath the blade 27 will be severed when the end of the instrument is moved in any preferred direction of cutting. As the end 22 of the instrument 10 is swept across the anterior capsule, the anterior capsule is progressively tensioned at the point of contact with the heel 26 which will follow the path made by the end of the instrument 22. The trailing blade portion 27 of the stylus 23 will progressively cut while the capsule is being tensioned by the heel 26. As a lateral force is imparted to the end of the instrument 22 to begin or maintain lateral movement, the heel 26 simultaneously pulls on the interior capsule in the same direction further tensioning the capsule. Although the heel 26 is depicted as being disposed laterally and above the sharp point 28, it is anticipated that it may be extended to the same level as the sharp point 28, or below it, so as to contact the anterior capsule first to create even more tension in the tissue.

From the foregoing, it can be realized that this invention provides an improved cutting instrument for surgery, and in particular, an improved rotating stylus cystitome for cataract operations. The cutting instrument provides smooth planar surfaces for permitting the rotating stylus to rotate and follow the distal end of the instrument as it is motioned in a predesigned configuration on the anterior capsule of an eye. Although various embodiments have been illustrated, this was for the purpose of describing, but not limiting the invention. Various modifications, which will become apparent to one skilled in the art, are within the scope of the invention described in the attached claims.

I claim:
1. A rotating stylus cystitome comprising:
    (a) an elongated rigid shaft having a central longitudinal axis and an end portion with an aperture transversely disposed therethrough, said end portion having a substantially planar surface disposed on a surgically superior surface of said shaft substantially perpendicularly to a central axis of said aperture; and
    (b) a cutting member comprising a swivel portion rotatably mounted to said shaft through said aperture and an outwardly facing knife portion laterally disposed from said swivel portion, said swivel portion comprising a superior end disposed to slide against said substantially planar surface to provide smoother rotation to said cutting member as it rotates on the shaft;
    said cutting member further comprising a heel portion extending in a surgically inferior direction further from said central longitudinal axis than at least a portion of said knife portion.

2. The cystitome of claim 1 wherein said knife portion comprises a cutting blade terminating in a sharp point.

3. The cystitome of claim 2 wherein said heel portion is disposed to provide a tensile force in said tissue when engaged with said tissue for cutting.

4. The cystitome of claim 3 wherein said heel portion is disposed on said cutting member above said sharp point.

5. The cystitome of claim 3 wherein said heel portion is disposed on said cutting member below said sharp point.

6. The cystitome of claim 3 wherein said heel portion is disposed on said cutting member at about the same distance from said rigid shaft as said sharp point.

7. The cystitome instrument of claim 1 wherein said cutting member comprises a crimped portion disposed on a superior end of said cutting member, said crimped portion having a dimension larger than the diameter of said aperture.

8. The cystitome of claim 7 wherein said crimped portion is slidably disposed on said surgically superior surface of said end portion of said rigid shaft.

9. The cystitome of claim 8 wherein said end portion comprises an inferior surface which is a substantially planar surface.

10. The cystitome of claim 9 wherein said blade comprises a concave configuration between said heel and said sharp point.

11. The cystitome of claim 10 wherein said blade comprises at least two blade faces forming an acute angle therebetween.

12. The cystitome of claim 11, wherein said acute angle is less than about 50°.

13. The cystitome of claim 11 wherein said acute angle is less than about 40°.

14. The cystitome of claim 11 wherein said acute angle is less than about 30°.

15. The cystitome of claim 14 wherein a said blade comprises an outwardly facing convex portion disposed next to sharp point 16. The cystitome of claim 7 wherein said crimped portion is disposed in a recessed portion of said rigid shaft.

17. The cystitome of claim 1 wherein said shaft is cannulated; to provide fluids through the end of said shaft.

* * * * *

UNITED STATES PATENT AND TRADEMARK OFFICE
CERTIFICATE OF CORRECTION

PATENT NO. : 4,885,004

DATED : December 5, 1989

INVENTOR(S) : David S. Pao

It is certified that error appears in the above-identified patent and that said Letters Patent is hereby corrected as shown below:

Col. 2, line 47, delete "50" and insert therefor --50°--.

Signed and Sealed this

Eleventh Day of June, 1991

Attest:

HARRY F. MANBECK, JR.

Attesting Officer

Commissioner of Patents and Trademarks